United States Patent [19]

Ogawa et al.

[11] Patent Number: 5,372,888

[45] Date of Patent: * Dec. 13, 1994

[54] CHEMICALLY ADSORBED FILM AND METHOD OF MANUFACTURING THE SAME

[75] Inventors: Kazufumi Ogawa, Hirakata; Norihisa Mino, Settu; Mamoru Soga, Osaka, all of Japan

[73] Assignee: Matsushita Electric Industrial Co., Ltd., Osaka, Japan

[*] Notice: The portion of the term of this patent subsequent to Feb. 5, 2009 has been disclaimed.

[21] Appl. No.: 831,486

[22] Filed: Feb. 5, 1992

[30] Foreign Application Priority Data

Feb. 6, 1991 [JP] Japan .................. 3-038134
Apr. 30, 1991 [JP] Japan .................. 3-098902

[51] Int. Cl.⁵ .................. B32B 15/08; B32B 17/10
[52] U.S. Cl. .................. 428/422; 428/429; 428/463
[58] Field of Search .................. 428/7, 422, 429, 463; 361/323; 252/573; 29/25.42

[56] References Cited

U.S. PATENT DOCUMENTS

| | | | |
|---|---|---|---|
| 4,539,061 | 9/1985 | Sagiv | 428/420 X |
| 4,673,474 | 6/1987 | Ogawa | 428/910 X |
| 4,863,794 | 9/1989 | Fujii et al. | 428/421 X |
| 4,902,585 | 2/1990 | Ogawa et al. | 428/900 X |
| 5,103,371 | 4/1992 | Ogawa et al. | 29/25.42 X |
| 5,143,750 | 9/1992 | Yamagata et al. | 427/436 X |
| 5,147,684 | 9/1992 | Tamura et al. | 428/695 X |
| 5,186,986 | 2/1993 | Ogawa | 428/1 |
| 5,187,639 | 2/1993 | Ogawa et al. | 29/25.42 X |
| 5,240,774 | 8/1993 | Ogawa et al. | 428/422 X |
| 5,284,707 | 2/1994 | Ogawa et al. | 428/419 X |

FOREIGN PATENT DOCUMENTS

0363924 10/1989 European Pat. Off. .
0386784  3/1990 European Pat. Off. .

OTHER PUBLICATIONS

World Patents Index Latest, Derwent Publications Ltd., London, GB; AN 86-065417 & JP-A-61 016 910 (Hitachi Cable KK), Jan. 24, 1986 (abstract).
World Patents Index, Week 50, Derwent Publications, Ltd., London, GB; AN 77-88959Y & JP-A-52 130 662 (Suwa Seikosha K.K. & Hamasawa Kogyo K.K.), 2 Nov. 1977.
Patent Abstracts of Japan, vol. 14, No. 152 (M-953)23 Mar. 1990 & JP-A-2 015 101 (Matsushita Electric Ind. Co.) 18 Jan. 1990.

*Primary Examiner*—Henry F. Epstein
*Attorney, Agent, or Firm*—Fish & Richardson

[57] ABSTRACT

Disclosed is an ornament with a thin film formed on the ornament surface. The thin film includes a fluorocarbon-based adsorbed monomolecular film, and the thin film is covalently bonded to the ornament. By contacting the ornament with the non-aqueous solution containing a chlorosilane group at one end and a fluorocarbon chain at the other end, a reaction occurs between hydroxyl groups at the ornament surface and the chlorosilyl groups of the material having a plurality of chlorosilyl groups. A monomolecular film which is covalently bonded to the ornament surface is thereby obtained. A thin, fluorine-containing, monomolecular film thus can be formed on the ornament such that it is chemically bonded to the ornament. The film is anti-contaminating, water- and oil-repelling, durable and does not spoil the intrinsic luster of the ornament.

3 Claims, 3 Drawing Sheets

CHEMICALLY ADSORBED FILM AND METHOD OF MANUFACTURING THE SAME

FIELD OF THE PRESENT INVENTION

This invention relates to forming a chemically adsorbed film on a substrate surface via siloxane bonds and a method of manufactering the same. More particularly, this invention relates to a film which is adsorbed to an ornament or polymer resin substrate surface, said film preferably being a fluorine-based film. This invention further relates to a method of adsorbing film to a substrate surface.

BACKGROUND OF THE INVENTION

In various fields, there is a demand for improving the surface of such materials as plastics, metals, ceramics, fibers, wood, concrete and coatings to meet various purposes.

For example, it has been well known in the art to improve the surface of polymers. For example, a surface can be made water- and oil-repelling by coating it with a fluorine-containing silane coupling material. To make a surface hydrophilic, it can be coated with polyvinyl alcohol. To make a surface anti-contaminating it can be coated with a suspension of a fluorocarbon-based polymer.

However, conventionally obtained coating films are weakly bonded to polymer-containing materials or coated substrates and become separated by repeatedly wiping the surface with a cloth or washing the surface with water. This results in a less of the beneficial effects of the surface treatment. Morecver, the conventional coating films comprise randomly oriented molecules. Therefore, the films have many pin holes which deteriorate their characteristics. Further, fluorocarbon-based polymer coating films lack transparency and can not be used on materials such as ornaments, and transparent plastic optical materials for which transparency is strongly demanded.

It is therefore, an object of the invention to provide a method of manufacturing a highly durable, highly functional chemically adsorbed film, which can solve the problems noted above that are inherent in the prior art.

The invention further concerns ornaments. More specifically, high performance ornaments which are highly water- and oil-repelling and anti-contaminating.

Ornaments, when contaminated, decrease in value and esteem. For ornaments, prevention of contaminants is most important. This applies to ornaments in actual use as well as those displayed in department store show windows.

Heretofore, there has been no effective way to prevent contamination of ornaments.

Scrupulous wiping or washing of ornaments is very time-consuming, and certain kinds of contaminants can not be readily removed without causing scars or scratches on the material.

Another object of the invention is to provide a high performance ornament which has an anti-contaminating effect. This is, contaminants will not attach, or they can be readily removed if attached.

SUMMARY OF THE INVENTION

An objective of the invention is to provide a chemically adsorbed monomolecular film bonded to an ornament surface, the film comprising a fluorocarbon group, wherein the film is covalently bonded to the ornament surface.

It is preferable in this invention that the fluorocarbon group containing chemically adsorbed monomolecular film is formed on the ornament substrate surface via a siloxane-based monomolecular film.

It is preferable in this invention that the ornament is selected from the group consisting of gem, pearl, watch, watch case, sapphire, ruby, emerald, garnet, cat's eye, diamond, topaz, quarz, crystal, agate, glass, silver, copper, aluminum, titanium, tin, stainless steel, precious metal, metal alloys, pottery, porcelain, ceramics, glass, stone, wood, and plastic.

Another objective of this invention is to provide a method of forming a chemically adsorbed film on an ornament surface, comprising washing the ornament and dipping the ornament in a solution obtained by dissolving a chlorosilane-based surface active material having a chlorosilane group at one end and a fluorocarbon group at the other end in an organic solvent. thereby forming a chemically adsorbed monomolecular film of the surfacre active material on the entire surface of the ornament.

It is preferable in this invention that the chlorosilane-based surface active matertial having a chlorosilane group at one end and a fluorocarbon straight chain group at the other end is

$CF_3-(CF_2)_m-R-SiX_pCl_{3-p}$ where m represents 0 or an integer, R represents an alkyl group, an alkylene group or an alkyne group or a substituted group containing a —Si— group or an oxygen atom, X represents a hydrogen atom or an alkyl group or a substituted group containing a —Si— group or an oxygen atom, and p represents 0, 1 or 2.

Another objective of this invention is to provide a method of laminating a chemically adsorbed film to an ornament surface, comprising washing the ornament, contacting the ornament with a non-aqueous solution containing an inner layer material having a plurality of chlorosilyl groups, thereby causing a reaction between hydroxyl groups at the surface of the ornament and chlorosilyl groups of the inner layer material having a plurality of chlorosilyl groups to precipitate the material on the surface of the ornament, removing an excess of the material from the ornament surface using a non-aqueous solution, reacting the inner layer material with water, and chemically adsorbing a chlorosilane-based surface active material having a chlorosilane group at one end and a straight chain fluorocarbon group at the other end to the ornament to form a laminated, chemically adsorbed monomolecular film.

It is preferable in this invention that the inner layer material containing a plurality of chlorosilyl groups is $SiCl_4$, $SiHCl_3$, $SiH_2Cl_2$, or $Cl(SiCl_2O)_nCl_3$ where n represents an integer from 1 to 20.

It is preferable in this invention that the chlorosilane-based surface active matetrial having a chlorosilane group at one end and a fluorocarbon chain group at the other end is $CF_3-(CF_2)_m-R-SiX_pCl_{3-p}$ where m represents 0 or an integer, R represents an alkyl group, an alkylene group or an alkyne group or a substituted group containing a —Si— group or an oxygen atom, X represents a hydrogen atom or an alkyl group or a substituted group containing a —Si— group or an oxygen atom, and p represents 0, 1 or 2.

Another objective of this invention is to provide a method of adsorbing a chemically adsorbed film containing siloxane bonds to a substrate surface comprising contacting the substrate surface with a mixed solution containing at least a chlorosilane-based surface active material and a fluorine-containing non-aqueous solution without active hydrogen and which is capable of reacting with the chlorosilane-based sufrface active material.

It is preferable in this invention that the fluorine-containing non-aqueous solution contains a tertiary amine or cyclic ether.

It is preferable in this invention that the substrate surface is treated with a member of the group consisting of dichlorosilane, trichlorosilane and tetrachlorosilane prior to forming the chemically adsorbed film.

It is preferable in this invention that the substrate surface is a polymer containing or coating substrate.

DETAILED DESCRIPTION OF THE INVENTION

This invention is an ornament with a thin film formed on the ornament surface. The thin film includes a fluorocarbon-based adsorbed monomolecular film, and the thin film is covalently bonded to the ornament surface. By contacting the ornament with the non-aqueous solution containing a chlorosilane group at one end and a fluorocarbon chain at the other end, a reaction occurs between hydroxyl groups at the ornament surface and the chlorosilyl groups of the material having a plurality of chlorosilyl groups. A monomolecular film which is covalently bonded to the ornament surface is thereby obtained. A thin, fluorine-containing, monomolecular film thus can be formed on the ornament such that it is chemically bonded to the ornament. The film is anti-contaminating, water- and oil-repelling, durable and does not spoil the intrinsic luster of the ornament.

According to the invention. a chemically adsorbed film is formed on a material or substrate surface via siloxane bonds. It is thus possible to obtain a highly durable, highly functional chemically adsorbed film compared to those in the prior art. In addition, a fluorine-containing non-aqueous solution not containing any active hydrogen capable of reacting with chlorosilane-based surface active material is used. Thus, it is possible to obtain a monomolecular film which is substantially pin-hole free and has a high density without any damage.

Further, according to a preferred embodiment of the invention, the fluorine-containing non-aqueous solution contains a tertiary amine or cyclic ether. Thus, the highly functional chemically adsorbed film may be formed without dissolving the substrate even if the substrate is a material such as an ornament, a polymer, a resin or a coating.

In a further preferred embodiment of the invention, prior to a reaction step to form the chemically adsorbed film, the substrate surface is treated with a material having a plurality of chrolosilyl groups such as dichrolosilane, trichlorosilane or tetrachlorosilane. It is thus possible to provide silonxane bonds at a high density to the substrate surface.

In yet a further preferred embodiment of the invention, the substrate surface is a polymer compound. It is thus possible to form the highly functional chemically adsorbed film according to the invention on a polymer compound surface which has been comparatively difficult in the prior art.

In the method according to the invention, various substrates can be used, for example plastics, metals, ceramics, fibers, wood, concrete and coatings. In the foregoing description, a polymer material is preferred as the substrate. The invention can be widely applied to the following polymer surfaces.

Examples of resin(s): a polyolefin such as a polypropylene and polyethylene, a polyvinylchloride plastic, a polyamide, a polyimide, a polyamideimide, a polyester, an aromatic polyester, a polycarbonate, a polystyrene, a polysulfide, a polysulfone, a polyethersulfone, a polyphenylenesulfide, a phenolic resin, a furan resin, a urea resin, an epoxy resin, a polyurethane, a silicon resin, an ABS resin, a methacrylic resin, an acrylate resin, a polyacetal, a polyphenylene oxide, a polymethylpentene, a melamine resin, an alkyd resin, an unsaturated polyester cured resin and the like. Thus, any general-purpose plastic material may be used. Such plastic material may contain a filler, e.g., carbon dioxide, calcium carbonate and titanium oxide, or a plastisizer, e.g., dibutyl phthalate. Further, it may be colored with a dye or a pigment.

Where it is desired to form a polymer composition that is water- and oil-repelling or anti-contaminating or slippery, an alkyl fluoride-containing chlorosilane surface active material is used as a material for forming the chemically adsorbed film. When it is desired to form a polymer composition according to the invention that is super-hydrophilic, after forming a chemically adsorbed film by using a chlorosilane-based surface active material which contains an alkyl group with an end vinyl group, the end is converted into a hydroxyl group by irradiating the film with an electron beam, X-rays, gamma ways, ultraviolet rays, etc. in an oxygen atmosphere. For example, a chemically adsorbed film is formed by using tetrachlorosilane and then reacting with water to convert the chlorosilyl bonds to silanol bonds.

Examples of the chlorosilane-based surface active material having an alkyl fluoride group are such trichlorosilane-based surface active materials as $CF_3(CH_2)_rSiX_pCl_{3-p}$,
$CF_3(CF_2)_sO(CH_2)_tSiX_pCl_{3-p}$,
$CF_3(CF_2)_uSi(CH_3)_2(CH_2)_vSiX_pCl_{3-p}$,
and $CF_3COO(CH_2)_wSiX_pCl_{3-p}$, where r is from 1 to 25, s is from 0 to 12, t is from 1 to 20, u is from 0 to 12, v is from 1 to 20, w is from 1 to 25. These surface active materials are suitably represented by the following examples:

$CF_3CH_2O(CH_2)_{15}SiCl_3$,
$CF_3(CF_2)_2Si(CH_3)_2(CH_2)_{15}SiCl_3$,
$CF_3(CH_2)_2Si(CH_3)_2(CH_2)_{15}SiCl_3$,
$CF_3(CF_2)_2Si(CH_3)_2(CH_2)_6SiCl_3$,
$CF_3(CF_2)_3(CH_2)_2Si(CH_3)_2(CH_2)_9SiCl_3$,
$CF_3COO(CH_2)_{15}SiCl_3$,
$CF_3(CF_2)_9(CH_2)_2SiCl_3$,
$CF_3(CF_2)_7(CH_2)_2SiCl_3$, and
$CF_3(CF_2)_5(CH_2)_2SiCl_3$ etc.

Particularly, trichlorosilane-based surface active materials are suitable because chlorosilyl bonds, other than those coupled to their hydrophilic groups, form intermolecular bonds with adjacent chlorosilane groups and with siloxane bonds. This forms a firmer chemically adsorbed film. Further, a trichlorosilane surface active material of the formula $CF_3(CF_2)_n(CH_2)_2SiCl_3$ where n represents an integer, most suitably 3 to 25, is preferred. This compound has a desirable solubility and chemically adsorption property. It is also water-repelling, anti-contaminating and has other desirable functional properties. Further, with an ethylene or acetylene group added to or incorporated in the alkyl fluoride chain portion, the chemically adsorbed film may be crosslinked after formation by irradiating it with an electron beam of about 5 Mrads, thereby further improving the hardness of the chemically adsorbed film.

Examples of the chlorosilane-based surface active material containing an alkyl group are such trichlorosilane-based surface active materials as $CH_3(CH_2)_rSiX_pCl_{3-p}$,
$CH_3(CH_2)_sO(CH_2)_tSiX_pCl_{3-p}$,
$CH_3(CH_2)_uSi(CH_3)_2(CH_2)_v SiX_pCl_{3-p}$,
and $CH_3COO (CH_2)_w SiX_pCl_{3-p}$, where r is from 1 to 25, s is from 0 to 12, t is from 1 to 20, u is from 0 to 12, v is from 1 to 20, w is from 1 to 25. These surface active materials are suitably represented by the following examples:

$CH_3CH_2O(CH_2)_{15}SiCl_3$,
$CH_3(CF_2)_2Si(CH_3)_2(CH_2)_{15}SiCl_3$,
$CH_3(CH_2)_2Si(CH_3)_2(CH_2)_{15}SiCl_3$,
$CH_3(CH_2)_2Si(CH_3)_2(CH_2)_6SiCl_3$,
$CH_3(CH_2)_5Si(CH_3)_2(CH_2)_9SiCl_3$,
$CH_3COO (CH_2)_{15}SiCl_3$,
$CH_3(CH_2)_9(CH_2)_2SiCl_3$,
$CH_3(CH_2)_7(CH_2)_2SiCl_3$, and
$CH_3(CH_2)_5(CH_2)_2SiCl_3$ etc.

and such lower-alkyl substituted monochlorosilane- or dichlorosilane-based surface active materials. Particularly, $CH_3(CH_2)_nSiCl_3$ where n represents an integer, most suitably 3 to 25, is preferable because of its desirable solubility. Further, the alkyl group in the chlorosilane-based surface active material may contain an end vinyl group as in the formula $CH_2=CH—(CH_2)_nSiCl_3$ where n represents an integer, preferably 3 to 25.

The chlorosilane-based surface active material according to the invention is not limited to those in the form of a straight chain as noted above. It is possible to use those in a form having a branched alkyl fluoride or hydrocarbon group or those in a form having a substituted alkyl fluoride or hydrocarbon group for silicon at one end (i.e., those represented by a formula $R_2SiCl_2$, $R_3SiCl$, $R^1R^2SiCl_2$ or $R^1R^2R^3SiCl$ where R, $R^1$, $R^2$ and $R^3$ represents an aklyl fluoride or hydrocarbon group). To increase the adsorption density, however, the straight chain form is preferred.

Further, by chemically asdorbing a material for forming an inner layer material having a plurality of chlorosilyl groups, e.g., $SiCl_4$, $SiHCl_3$, $SiH_2Cl_2$, and $Cl(SiCl_2O)_nCl_3$ (where n represents an integer in from 1 to 20), $SiCl_m(CH_3)_{4-m}$, $SiCl_m(C_2H_5)_{4-m}$ (where m represents 1, 2 or 3), and $HSiCl_p(CH_3)_{3-p}$, $HSiCl_p(C_2H_5)_{3-p}$ (where p represents 1 or 2), and then reacting it with water, surface chlorosilyl bonds are converted to hydrophilic silanol bonds, thereby making the polymer composition hydrophilic. Among the materials containing a plurality of chlorosilyl groups, tetrachlorosilane ($SiCl_4$) is suitable in that it is highly reactive and low in molecular weight, thus providing silanol bonds at a high density. In this way, the polymer composition may be made highly hydrophilic compared to the case of oxidizing a polymer-containing or a polymer coating material. The polymer composition is thus made super-hydrophilic and may be used in situ. A chlorosilane-based surface active material containing an alkyl fluoride group may be chemically adsorbed to the polymer. A chemically adsorbed film obtained in this way has a high density and has enhanced water- and oil-repelling and anti-contaminating properties.

The substrate according to the invention is by no means limited so long as its surface contains active hydrogen groups such as —OH, —COOH, —NH$_2$ or =NH groups.

The polymer composition is obtained according to the invention by a method which comprises a step of making a polymer-containing material surface hydrophilic by oxidization, and a step of making a chemically adsorbed film containing siloxane bonds by chemically adsorbing a chlorosilane-based surface active material on the oxidized surface by dipping the surface in a fluorine-containing non-aqueous solution.

The polymer-containing material may be oxidized by the usual means, e.g., an oxygen plasma treatment, a corona treatment or a method of dipping the material in a blend solution containing concentrated sulfuric acid and potassium dichromate (i.e., a chromium blend liquid treatment).

As the fluorine-containing non-aqueous solution for the method of obtaining a polymer composition according to the invention may be any solution which does not permit dissolution of a polymer contained in the material with a chemically adsrobed film to be formed thereon and is free from active hydrogen capable of reacting with the chlorosilane-based surface active material. Suitable examples are tertiary amine containing a fluoroalkyl group or a cyclic ether having a fluoroalkyl group. Examples of the tertiary amine are $N(C_nF_{2n+1})_3$ where n represents an integer from 2 to 10, the fluoroalkyl group being either straight or branched. Examples of the cyclic ether are those having the formula:

(where m represents an integer from 2 to 8, n represents an integer from 0 to 10)

As the chemically adsorbed film formed on the surface of a polymer composition according to the invention, a single chemically adsorbed monomolecular layer is sufficient. To form only a single layer as a chemically adsorbed monomolecular film, it is only necessary to chemically adsorb the chlorosilane-based surface active material or a material containing a plurality of chlorosilyl groups and then wash away the non-aqueous solution without contact with moisture. No other specific process is needed. The chemically adsorbed film may of course be a laminated monomolecular film. Where the chemically adsorbed film includes a laminatied layer, the functional groups are oriented to improve the density and provide for high functional performance.

A typical embodiment of the invention is an ornament having a thin film formed on its surface. The thin film includes at least a fluorine-containing chemically adsorbed monomolecular layer which is chemically bonded to the ornament material. It is thus possible to obtain a highly anti-contaminating, high performance ornament, in which contaminants will not attach, or in which may be easily removed. Further, the ornament surface will have an improved smoothness with a high resistance to scars and scratches.

Further, according to the invention a fluorocarbon-based monomolecular film having a thickness in the nanometer range is formed on the ornament surface. Therefore, the luster intrinsic of the ornament is not spoild. The film is a carbon fluoride-based monomolecular film and has excellent water- and oil-repelling properties, brilliant surface, and provides an enhanced anti-contaminating effect. A high performance ornament thus can be provided which is highly water- and oil-repelling and anti-contaminating particularly with respect to sweat and dirt.

Further, the method as described above according to the invention permits efficient formation of a thin film according to the invention.

Ceramic or metal ornaments usually contain hydroxyl groups at their surface. Thus, a fluorocarbon-based lamination chemically adsorbed monomolecular film may be formed on the ornament surface by a method which comprises a step of contacting the ornament with a non-aqueous solution containing molecules, Where the molecules are straight carbon chain having a chlorosilane group ($SiCl_nX_{3-n}$, n representing 1, 2 or 3, X representing a functional group) at one end, e.g., a chlorosilane surface active material having a fluorocarbon group and a chlorosilane group for forming a monomolecular film on the ornament surface with a reaction caused between hydroxyl groups at the ornament surface and chlorosilyl groups of the material, or contacting the ornament with a non-aqueous solution containing a material having a plurality of chlorosilyl groups to precipitate the material having a plurality of chlorosilyl groups on the ornament surface with a reaction caused between hydroxyl groups at the ornament surface and chlorosilyl groups of the material, a step of washing away excess material having a plurality of chlorosilyl groups remaining on the ornament using a non-aqueous organic solvent followed by washing with water. Thus forming a siloxane-based monomolecular film of the material having a plurality of chlorosilyl groups on the ornament, and a step of forming a lamination chemically adsorbed monomolecular film by chemically adsorbing a silane-based surface active material having a straight carbon chain with a chlorosilane group at one end to the ornament.

Now, examples of the invention will be given.

EXAMPLE 1

A natural pearl 1 (FIG. 1) was dipped and held for about 2 hours in a non-aqueous solution containing a material having a fluorocarbon group and a chlorosilane gorup, e.g., "Fluorinert FC-40" (products by 3M corp., a fluorine-based solution) which was obtained by dissolving about 1 wt. % of

Figure 1:
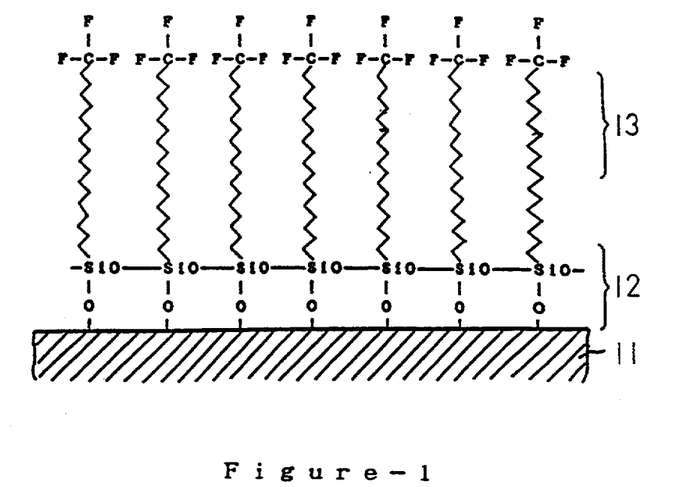
FIG. 1 is a perspective view showing a pearl as a typical example of ornament according to the invention.

Since the pearl is mainly composed of calcium carbonate and apachite, its surface contains numerous hydroxyl groups. Thus, a dehydrochlorination reaction was brought about between —SiCl groups of the material having a fluorocarbon group and a chlorsilane group and hydroxyl groups. This reaction is represented in the following formula [1].

Formula [1]

The pearl 1 was then washed by "Fluorinert FC-40" to remove unreacted material remaining on the surface, followed by washing with water or exposing to air containing moisture. The —SiCl group was changed to a —SiOH as in formula [2].

Formula [2]

Each silanol group (—SiOH) was then dehydrated and crosslinked to form a siloxane bond (—SiO—) after drying as in formula [3]. Drying temperature may be room temperature or above.

Formula [3]

Figure 3:
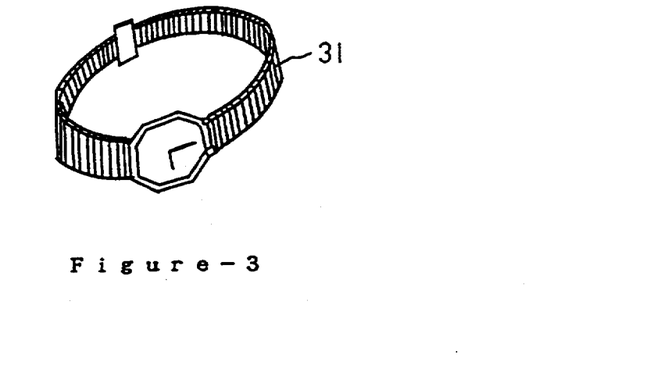
FIG. 3 is a schematic sectional view, enlarged to a molecular level, showing the surface of a pearl according to the invention.

An adsorbed monomolecular film 2 could be obtained on the surface of the pearl 1 as shown FIG. 3. The adsorbed monomolecular film 2 has a fluorine group and is chemically bonded (i.e., covalently bonded) to the pearl 1. The chemical bond is via a siloxane bond. The formation of chemically adsorbed monomolecular film 2 was measured by FTIR spectrometry and the thickness was about 1.5 nanometers (nm). It is firmly bonded such that it will not separate.

Similar monmolecular films can be similarly formed on ornaments of stainless steel, sapphire, ruby, emerald, garnet, cat's eye, diamond. topaz, quarz, crystal, agate, glass and such metals as silver, copper, aluminum, titanium, tin, etc. or alloys of these metals, with the surface covered by an oxide filim conaining hydroxyl groups. In this film formation, the adsorption time was adjusted appropriately. It had been thought that no natural oxide film was formed on the surface platinum and gold. Actually, however, the same effects as above can be obtained. This is presumably attributable to a very thin oxide film covering the surface.

The processed pearl was actually used to find that the attachment of contaminants can be greatly reduced compared to a non-processed pearl. Contaminants, if attached, can be easily removed by merely rubbing the surface with a brush with no scar or scratch being produced. Further, oily contaminants can be removed by merely washing with water. The luster of the petal did not lost when contacted with sweat or dirt.

EXAMPLE 2

Figure 2:
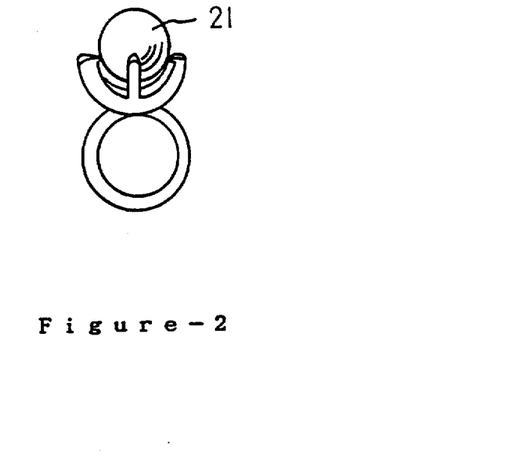
FIG. 2 is a perspective view showing a wrist watch as a typical ornament according to the invention.
Figure 4:
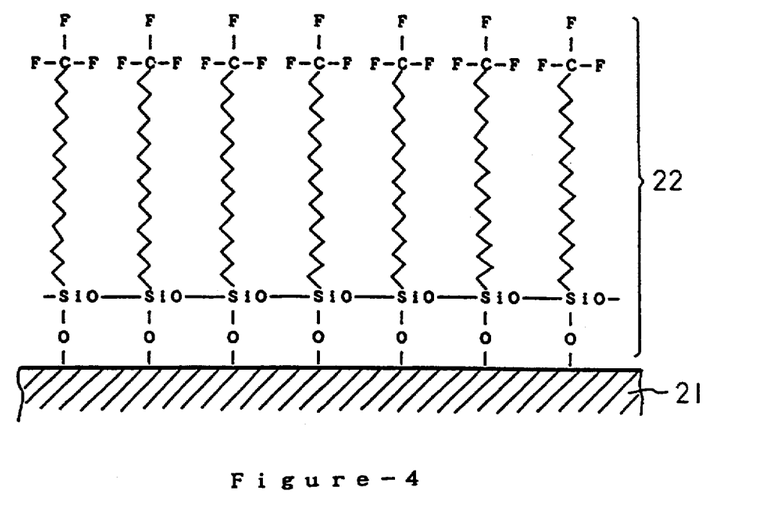
FIG. 4 is a schematic sectional view, enlarged to a molecular level, showing a wrist watch band surface embodying the invention.

As a metal ornament, which was hydrophilic but contained less hydroxyl groups, a stainless steel wrist watch band 11 (FIG. 2) was processed. The same effects are obtainable with glass frames made of such metals as titanium, aluminum, stainless steel and silver. The wrist watch band was dipped and held for 30 minutes in a solution prepared by dissolving 1% by weight of a material having a plurality of trichlorosilyl groups, e.g., $SiCl_4$, $SiHCl_3$, $SiH_2Cl_2$, or $Cl(SiCl_2O)_nCl_3$ (where n represents an integer in a range from 1 to 20) in a non-aqueous solvent, e.g., a chloroform solvent. $SiCl_4$ being particularly preferred since it is small in molecular size and active with respect to the hydroxyl groups, thus providing a wrist watch band surface which is uniformly hydrophilic. As a result, a hydrochloric acid removal reaction was brought about on the surface due to some —OH groups 12 present at the wrist watch band surface (FIG. 4). A chlorosilane monomolecular film of the material having a plurality of trichlorosilyl groups was thus formed.

By using $SiCl_4$ as the material containing a plurality of trichlorosilyl groups, for example, molecules represented by formulas 4 and/or 5.

Formula [4]

Formula [5]

were secured via —SiO— bonds to the surface through a hydrochloric acid removal reaction brought about on the surface due to a small amoullt of hydrophilic —OH groups exposed at the surface of the wrist watch band 11.

Figure 5:
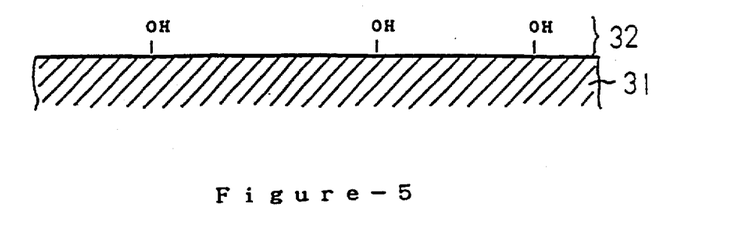
FIG. 5 is a schematic sectional view, enlarged to a molecular level, showing a wrist watch band surface during processing.

By subsequently washing with a non-aqueous solvent, e.g., chloroform. and then with water. unreacted $SiCl_4$ molecules were removed. A siloxane monomolecular film 13 represented by formulas 6 and/or 7 was obtained on the wrist watch band surface (FIG. 5).

Formula [6]

Formula [7]

The monomolecular film 13 obtained in this way was bonded by chemical bonds of —SiO— to the ornament and did not separate. In addition, its surface contains numerous —SiOH bonds, corresponding in number to about three times the initial number of hydroxyl groups.

Figure 6:
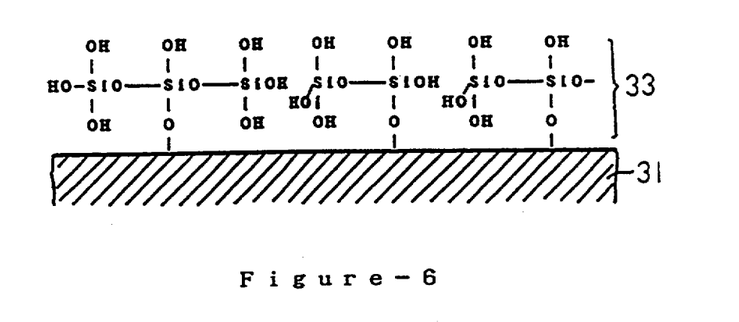
FIG. 6 is a schematic sectional view, enlarged to a molecular level, showing a wrist watch band surface after processing.

Further, the wrist watch band provided with the monomolecular flim having numerous —SiOH bonds at the surface, was dipped and held for about one hour in an aqueous solution containing a material having a fluorocarbon group and a chlorosilane group, e.g., a solution obtained by dissolving about 1 wt. % of $CF_3(CF_2)_7(CH_2)_2SiCl_3$ in a solvent containing 80 of n-hexadecane, 12% of carbon tetrachloride and 8% of chloroform, thus producing bonds of $CF_3(CF_2)_7(CH_2)_2Si(O—)_3$ on the wrist watch band surface. This reaction proceeded substantially the same as above in formulas [1] to [3]. A fluorine-containing monomolecular film 14 was formed. The film was chemically bonded to the inner siloxane monomolecular film 13 (FIG. 6). It was formed over the entire wrist watch band surface and had a thickness of about 1.5 nanometers. It did not separate in a peel-off test.

With an ethylene or acetylene group added to or incorporated in the carbone chain portion, the monomolecular film can be crosslinked after formation by irradiating it with an electron beam of about 5 Mrads, thus further improving hardness.

As has been shown in the above example, a carbon fluoride-based monomoecular film having a thickness at the nanometer level is formed on the ornament surface without spoiling the luster intrinsic to the ornament. This film has excellent water- and oil-repelling properties and makes the ornament surface anti-contaminating. It is thus possible to provide a high performance ornament which is highly anti-contaminating with respect to sweat and dirt. Moreover, this effect permits a great reduction in the number of times of washing.

EXAMPLE 3

Figure 7:
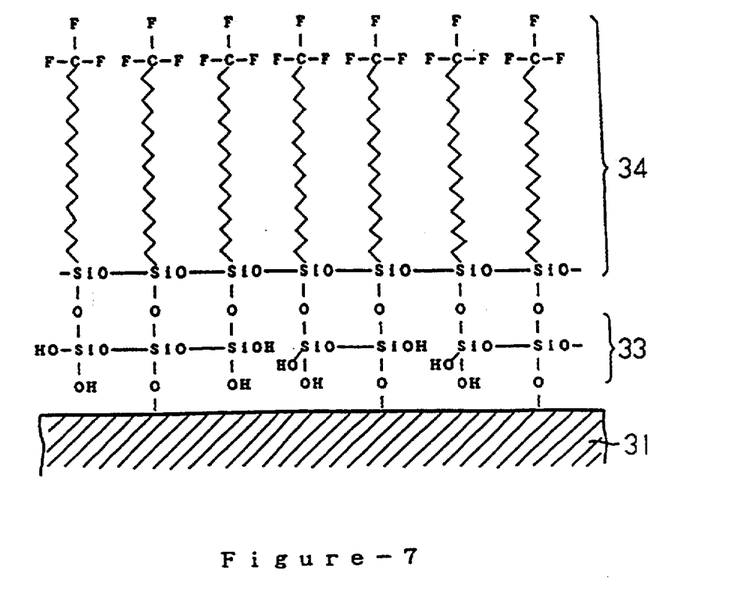
FIG. 7 is a sectional view showing a polymer composition obtainable by a method embodying the invention.

A polycarbonate substrate 21 (FIG. 7) (5 cm in each side and 0.3 cm in thickness) was subjected to an oxygen plasma treatment in a UV dry stripper ("UV-1" manufactured by Samco International) at an oxygen flow rate of 1 l/min. to oxidize the surface. The substrate was then dipped and held in a tri(n-nonafluorobutyl)amine solution containing $10^{-2}$ mol/l of heptadecafluorodecyltrichlorosilane used as the fluoroalkyl group-containing chlorosilyl-based surface active material in a nitrogen atmosphere at room temperature for 60 minutes. Unreacted heptadecafluorodecyltrichlorosilane was removed by washing with tri(n-nonafluorobutyl)amine solution and then washing with pure water. A fluoroalkyl group-containing chemically adsorbed monomolecular film 23 was formed on the polycarbonate substrate 21 via covalent siloxane bonds 22 (FIG. 7). This reaction proceeded substantially the same as above in formulas [1] to [3].

EXAMPLE 4

The same experiment was carried out as Example 3 except that an acrylic acid resin substrate was used in lieu of the polycarbonate substrate.

EXAMPLE 5

The same experiment was carried out as Example 3 except that a polypropyrene substrate was used in lieu of the polycarbonate substrate.

EXAMPLE 6

The same experiment was carried out as Example 3 except that an ABS resin substrate was used in lieu of the polycarbonate substrate.

EXAMPLE 7

The same experiment was carried out as in Example 3 except that a poly(ethylene terephthalate) (PET) substrate was used in lieu of the polycarbonate substrate.

EXAMPLE 8

The same experiment as carried out as in Example 3 except that tri(nonafluoroisobutyl)amine was used in lieu of tri(n-nonafluorobutyl)amine.

EXAMPLE 9

The same experiment was carried out as in Example 3 except that tri(nonafluoroisobutyl)amine was used in lieu of tri(n-nonafluorobutyl)amine in Example 4.

EXAMPLE 10

The same experiment was carried out as in Example 3 except that tri(nonafluoroisobutyl)amine was used in lieu of tri(n-nonafluorobutyl)amine in Example 5.

EXAMPLE 11

The same experiment was carried out as in Example 3 except that tri(nonafluoroisobutyl)amine was used in lieu of tri-(n-nonafluorobutyl)amine in Example 6.

EXAMPLE 12

The same experiment was carried out as in Example 3 except that tri(nonafluoroisobutyl)amine was used in lieu of tri(n-nonafluorobutyl)amine in Example 7.

EXAMPLE 13

The same experiment was carried out as in Example 3 except that 2-(n-nonafluorobutyl)perfluorofuran was used in lieu of tri-(n-nonafluorobutyl)amine in Example 3.

EXAMPLE 14

The same experiment was carried out as in Example 3 except that 2-(n-nonafluorobutyl)perflurofuran in lieu of (tri(n-nonafluorobutyl)amine in Example 4.

EXAMPLE 15

The same experiment was carried out as in Example 3 except that 2-(n-nonafluorobutyl)perfluorofuran was used in lieu of tri(n-nonafluorobutyl)amine in Example 5.

EXAMPLE 16

The same experiment was carried out as in Example 3 except that 2-(n-nonamofluoroutyl)perfluorofuran was used in lieu of tri(n-nonafluorobutyl)amine in Example 6.

EXAMPLE 17

The same experiment was carried out as in Example 3 except that 2-(nonafluorobutyl)perfluorofuran was uxed in lieu of tri(n-nonafluorobutyl)amine in Example 7.

EXAMPLE 18

The same experiment was carried out as in Example 3 except that a butadiene-styrene rubber substrate was used in lieu of the polycarbonate substrate in Example 3.

EXAMPLE 19

The same experiment was carried out as in Example 3 except that a butyl rubber substrate was used in lieu of the polycarbonate substrate in Example 3.

EXAMPLE 20

The same experiment was carried out as in Example 3 except that a nitrile rubber substrate was used in lieu of the polycarbonate substrate in Example 3.

EXAMPLE 21

The same experiment was carried out as in Example 3 except that a method of dipping and holding the substrate for 5 minutes in concentrated sulfuric acid containing 10% by weight of potassium dichromate was used in lieu of the method of oxidization.

COMPARATIVE EXAMPLE 1

A silane coupling material (i.e., a methanol solution containing 2% by weight of heptadecafluorodecyltrimethoxiysilane) was spin coated on a polycarbonate substrate surface and then dried at 20° C. for one hour.

COMPARATIVE EXAMPLE 2

A chemically adsorbed monomolecular film of heptadecafluorodecyltrichlorosilane was formed without oxidization of the polycarbonate substrate in Example 3.

COMPARATIVE EXAMPLE 3

A suspension of polytetrafluoroethylene was spray coated on the polycarbonate substrate surface in Example 3 and then thermally dried at 120° C. for one hour.

The contact angles of samples in Examples 3 to 21 and Comparative examples 1 and 2 were examined. The contact angle was measured right after formation of the chemically adsorbed film or coating film and after rubbing the film surface 10,000 times with water-wetted cloth. Table 1 shows the results.

TABLE 1

| | Contact angle (°) with respect to water | | Contact angle (°) with respect to salad oil | |
|---|---|---|---|---|
| | Initial value | After test | Initial value | After test |
| Example 3 | 121 | 119 | 101 | 99 |
| Example 4 | 131 | 128 | 112 | 109 |

TABLE 1-continued

| | Contact angle (°) with respect to water | | Contact angle (°) with respect to salad oil | |
|---|---|---|---|---|
| | Initial value | After test | Initial value | After test |
| Example 5 | 116 | 114 | 95 | 93 |
| Example 6 | 134 | 131 | 114 | 112 |
| Example 7 | 125 | 123 | 106 | 104 |
| Example 8 | 119 | 116 | 99 | 97 |
| Example 9 | 129 | 127 | 110 | 110 |
| Example 10 | 114 | 111 | 104 | 101 |
| Example 11 | 132 | 130 | 112 | 100 |
| Example 12 | 123 | 120 | 104 | 102 |
| Example 13 | 100 | 98 | 81 | 80 |
| Example 14 | 124 | 122 | 105 | 102 |
| Example 15 | 102 | 100 | 82 | 80 |
| Example 16 | 100 | 99 | 80 | 79 |
| Example 17 | 111 | 108 | 90 | 89 |
| Example 18 | 106 | 104 | 86 | 84 |
| Example 19 | 117 | 114 | 97 | 96 |
| Example 20 | 116 | 113 | 96 | 93 |
| Example 21 | 117 | 115 | 98 | 96 |
| Com. Ex. 1 | 93 | 45 | 61 | 12 |
| Com. Ex. 2 | 45 | 45 | 12 | 12 |

As observed from Table 1, the polymer compositions obtainable by the method according to the invention remained water- and oil-repelling or hydrophilic even after the surface had been rubbed repeatedly with water-wetted cloth. The sample of Comparative example 1, however, was no longer water- and oil-repelling. With the sample of Comparative example 2, which used a polymer composition without surface oxidization, it was impossible to form a chemically adsorbed film containing siloxane bonds.

The polymer composition with the chemically adsorbed monomolecular film containing a fluoroalkyl group formed on the surface had an excellent anti-contaminating property. After the friction test, the sample of Example 3 was dipped in salad oil. Its surface was then wiped with tissue paper. Oil could be easily wiped away. The sample in Comparative example 1 had a surface oil film and was sticky even after its surface had been wiped several times with tissue paper.

The polymer composition of the invention can also be utilized with optical materials. The light transmisson factor of the polycarbonate substrate in Example 3 with respect to visible light was 92%. With the sample of Comparative example 3, obtained by coating with polytetrafluoroethylene, the light transmission factor was reduced to 50% or below, and the transparency was considered inferior approximating that of stained glass.

The chemically adsorbed film mentioned above in each of the examples was a single monomolecular film. However, the same functions could be obtained on a polymer composition with a laminated chemically adsorbed monomolecular film or with a chemically adsorbed film formed without washing away unreacted chlorosilane-based surface active material. Further, in the above examples a relatively pure polymer substrate was used as the polymer-containing substrate, but the same functions of polymer composition could be obtained with polymers incorporating fillers, plastisizers, coloring agents, etc.

As shown above, according to the invention a polymer-containing substrate surface is subjected to an oxidization treatment to form hydroxyl or like hydrophilic groups. A chemically adsorbed film containing siloxane bonds is formed on the substrate surface by adsorbing a chlorosilane-based surface active material. Thus, a chemically adsorbed film can be readily formed without having any hydroxyl or like hydrophilic group as a repetition unit. In addition, a very high density chemically adsorbed film may be formed by merely diping a polymers-containing or coating substrate in a fluoroine-containing non-aqueous solution containing a chlorosilane-based surface active material. Thus, the chemically adsorbed film can be highly water- and oil-repelling, anti-contaminating or super-hydrophobic depending on the function of the chlorosilane-based surface active material used.

As has been shown, since the polymer composition according to the invention is provided with a chemically adsorbed film containing siloxane bonds formed on the surface, excellent durability with respect to repeated washing can be obtained compared to that in the prior art. When the chemically adsorbed film contains a fluorocarbon group, it is highly water- and oil-repelling and anti-contaminating.

Further, with the method of obtaining a polymer composition according to the invention, by preliminarily oxidizing the polymer composition surface, a chemically adsorbed film containing siloxane bonds can be formed by chemically adsorbing a chlorosilane-based surface active material.

As has been shown, the invention is greatly beneficial to industry.

The invention may be embodied in other specific forms without departing from the spirit or essential characteristics thereof. The present embodiment is to be considered in all respects as illustrative and not restrictive, the scope of the invention being indicated by the appended claims rather than by the foregoing description and all changes which come within the meaning and range of equivalency of the claims are intended to be embraced therein.

We claim:

1. A chemically adsorbed monomolecular film covalently bonded to a surface of an ornamental substrate, said film comprising a fluorocarbon straight chain group of the formula $CF_3-(CF_2)_m-R-SiX_pCl_{3-p}$, where m represents 0 or an integer, R represents an alkyl group, an alkylene group, an alkyne group or a substituted group containing a —Si— group or an oxygen atom, X represents a hydrogen atom or an alkyl group or a substituted group containing a —Si— group or an oxygen atom, and p represents 0, 1 or 2.

2. The chemically adsorbed film according to claim 1, wherein said chemically adsorbed monomolecular film is formed on said ornamental substrate surface via a siloxane-based monomolecular film.

3. The chemically adsorbed film according to claim 1, wherein said ornamental are substrates selected from the group consisting of a gem, pearl, watch, watch case, sapphire, ruby, emerald, garnet, cat's eye, diamond, topaz, quartz, crystal, agate, glass, silver, copper. aluminum, titanium, tin, stainless steel, precious metal, metal alloys, pottery, porcelain, ceramics, glass, stone, wood, and plastic.

* * * * *